United States Patent [19]
Bohannon

[11] Patent Number: 5,429,234
[45] Date of Patent: Jul. 4, 1995

[54] OPERATING ROOM SPONGE-RECEIVING BAG STRIP

[75] Inventor: George A. Bohannon, Louisville, Ky.

[73] Assignee: Weist Industries Inc, Louisville, Ky.

[21] Appl. No.: 141,586

[22] Filed: Oct. 27, 1993

Related U.S. Application Data

[63] Continuation of Ser. No. 772,154, Oct. 7, 1991, abandoned.

[51] Int. Cl.⁶ .............................................. B65D 30/00
[52] U.S. Cl. .................................. 206/362; 206/363; 383/38
[58] Field of Search ............... 206/363, 370, 362, 438, 206/459; 383/38–40

[56] References Cited

U.S. PATENT DOCUMENTS

| | | | |
|---|---|---|---|
| 3,749,237 | 7/1973 | Dorton | 206/438 |
| 4,361,231 | 11/1982 | Patience | 383/39 |
| 4,422,548 | 12/1983 | Chessman et al. | 206/438 |
| 4,887,715 | 12/1989 | Spahn et al. | 206/438 |
| 5,048,683 | 9/1991 | Westlake | 206/438 |

Primary Examiner—Jimmy G. Foster

[57] ABSTRACT

Operating room sponge retainer device including a flexible planar base having a selected number of pockets on one side of the base. Each pocket receives a sponge during the course of an operating procedure. A receiving pocket is provided at, at least one end of the device on the either side of the plane of the device and adapted to receive a portion of the device above the pocket where the portion is rolled and inserted into the receiving pocket.

8 Claims, 3 Drawing Sheets

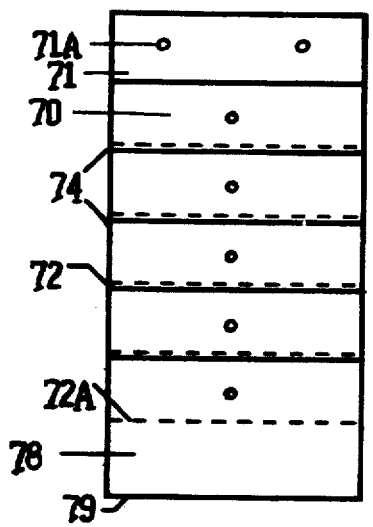
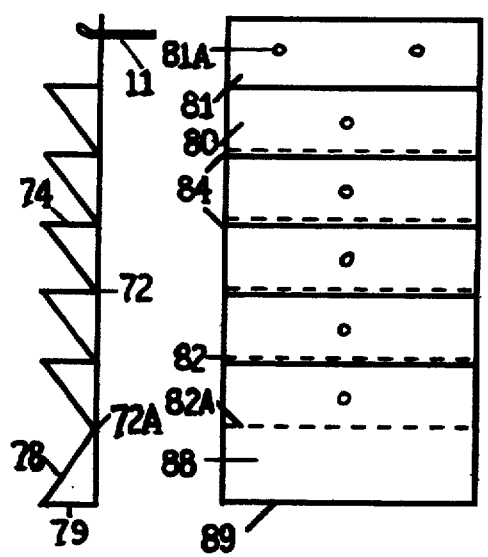
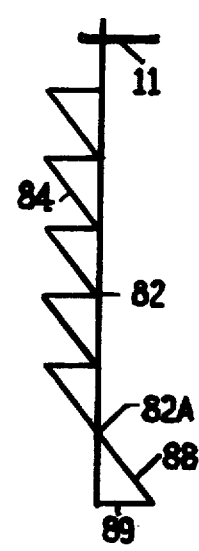
Fig 6A    Fig 6B    Fig 7A    Fig 7B
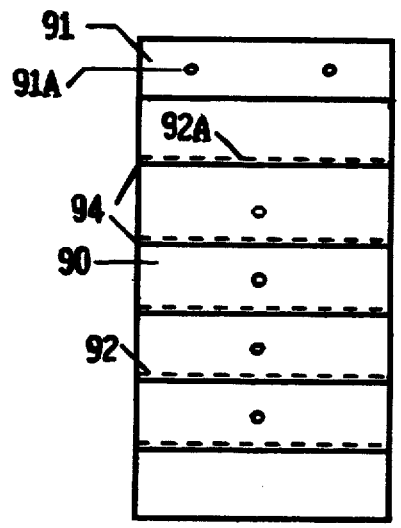
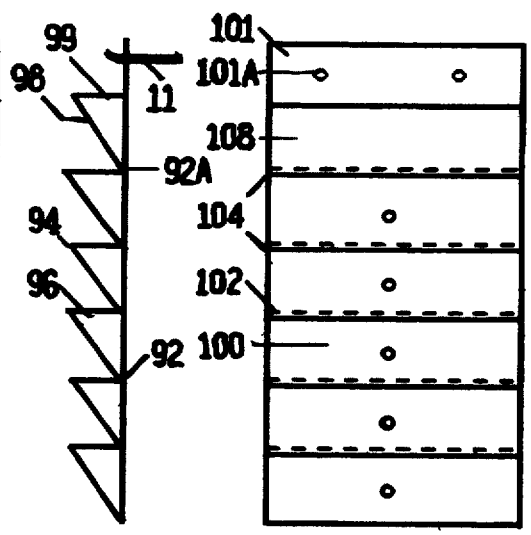
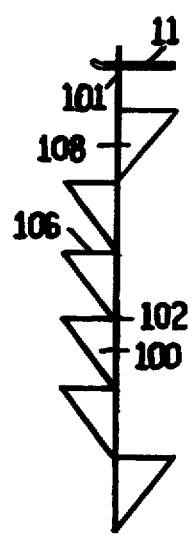
Fig 8A    Fig 8B    Fig 9A    Fig 9B

OPERATING ROOM SPONGE-RECEIVING BAG STRIP

The present application is a continuation of my application Ser. No. 07/772,154, filed Oct. 7, 1991, abandoned.

BACKGROUND OF THE INVENTION

The present invention relates to a method and apparatus for maintaining accountability of surgical sponges during an operating procedure and for effectively retaining the sponges for disposal subsequent to the operating procedure.

During the course of an operating procedure numerous sponges, which can be gauze like pads, are utilized to absorb blood resulting from the surgical wound to maintain suitable conditions in the wound for the operation. Such sponges are of significant importance to the operating procedure but it is equally important that all such sponges be removed by the end of the procedure.

Procedures have been adopted for the counting of the number of sponges present at the beginning of the operating procedure and confirming the count at the end of the procedure in order to assure that no sponges have been left in the operating wound. One apparatus and procedure for accomplishing the objective is disclosed in U.S. Pat. No. 3,749,237 wherein a bag arrangement is provided so that the sponges can be located in pockets provided in the device which is hung on a scale for both visual and weight accounting of the sponges.

Prior to the use of the device shown in U.S. Pat. No. 3,749,237 the most common procedure provided for depositing soil sponges in groups on a uniform number of folded towels or sheets layed on a table or the floor of the operating room. The approach consummed considerable space and allowed dirty sponges to be exposed to the atmosphere of the operating room for long periods of time which could result in bacterial contamination of the atmosphere.

The recognition of significant infectious blood diseases as such acquired immune deffiency syndrome (AIDS) has resulted in even more concern over the open exposure of blood in operating rooms and elsewere.

Device within the scope of U.S. Pat. No. 3,749,237 operated satisfactorily however, the leakage of blood during the preparation of the devices including the sponges for disposal has come to be a problem both because of the increasing occurrence of infectious blood diseases and from the standpoint of the necessity for cleaning the operating room.

No prior art devices known which accomplishes the objective of the restriction of the lost of blood and to facilitate the cleaning of the operating room.

SUMMARY OF THE INVENT ION

The present invention provides a new, useful and highly effective means for handling soiled sponges during an operating procedure. More particularly, devices within the scope of the present invention provide a highly improved means for preparing the package of sponges for disposal in post-operative periods.

Devices within the scope of the present invention are economical for the manufacturer, effective in use and particularly effective in the disposal of soiled surgical sponges.

Briefly, the present invention provides an operating room sponge retainer device including a flexible planar base having a selected number of pockets ion one side of the base. Each pocket receives a sponge during the course of an operating procedure. A receiving pocket is provided at at least one end of the device on either side of the plane of the device and adapted to receive a portion of the device above the pocket where the portion is rolled and inserted into the receiving pocket.

Examples of arrangements within the scope of the present invention are illustrated in the accompanying drawings and described hereinafter but it will be understood that the illustrations provided and the descriptions given are not by way of limitation but are by of example only.

BRIEF DESCRIPTIONS OF THE DRAWINGS

Examples of arrangements within the scope of the present invention are illustrated in the accompanying drawings wherein:

FIGS. 6A–6B illustrate yet another arrangement within the scope of the present invention;

FIGS. 7A–7B illustrate another arrangement within the scope of the present invention;

FIGS. 8A–8B illustrate another arrangement within the scope of the present invention;

FIGS. 9A–9B illustrate another arrangement with the scope of the present invention;

DETAILED DESCRIPTION OF THE DRAWINGS

Figure 1A:
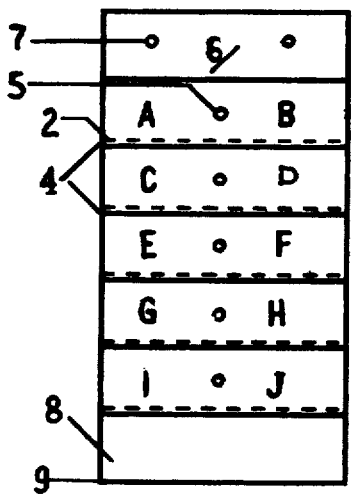
FIGS. 1A, 1B illustrate one arrangement within the scope of the present invention.

Referring now to the drawings which illustrate examples of arrangements within the scope of the present invention, in each case a series of pockets are provided on a planar base to be hung vertically from a support. The pockets are adapted to receive used surgical sponges and to retain the sponges during an operating procedure for accounting. Several of the packages of retainers may be utilized during a course of an operation but in each case the devices can be utilized and visual expection can be provided to assure accountability for all the sponges utilized. While the devices within the scope of the present invention illustrated in the Figures are illustrated in a planar form it will be understood that the devices can be formed on a roll and than separated for individual use still allowing the advantages of shipment of the devices in rolled form.

Figure 1B:
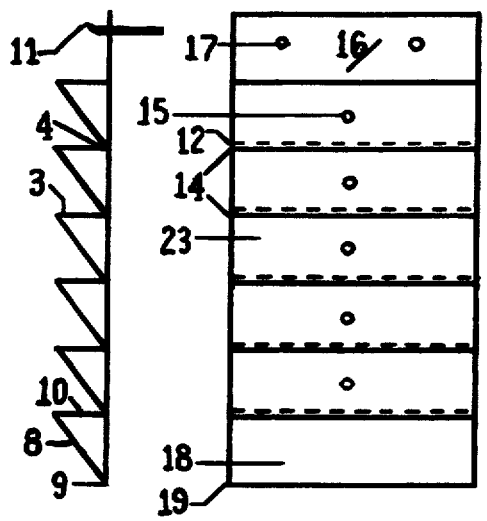

Referring now to FIGS. 1A and 1B, a continuous length of bag strips is provided with uniformly spaced transverse slits 4 provided between each bag strip 1. A seal 2 is provided at the bottom of each bag strip. A weld 5 can be provided intermediate each bag strip 1 to divide the bag strip in two pockets. The weld 5 can be broken in the event that it becomes desirable to utilize a larger sponge which occupies more space than one pocket. In the arrangement shown an upper panel 6 is provided with perforated holes 7 to receive a support 11 as shown. In common practice the support 11 can be mounted to a wall support (not shown) or can be carried by a scale in the event the procedure calls for the weighing of the material prior to disposal.

In any event the support 11 is inserted through the holes 7 to hold the bag assembly is a vertical direction as shown. Slits 4 are provided to define pockets 3 in each of the bag sections.

Figure 3A:
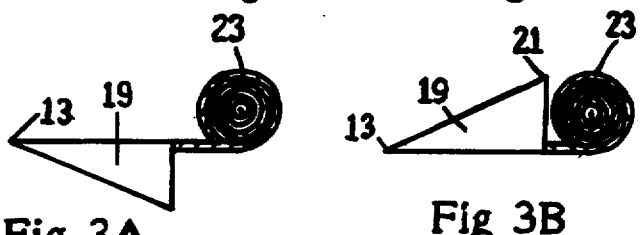
FIGS. 3A–3C illustrate operation of examples of device within the scope of the present invention.
Figure 3B:
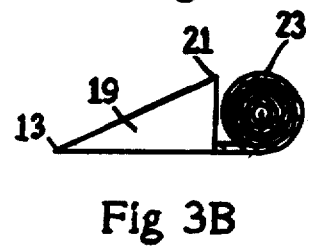
Figure 3C:
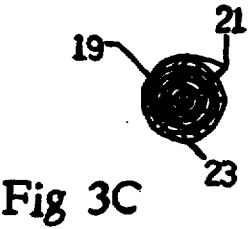

In accordance with one feature of the present invention a receiving pocket 8 is provided having a bottom seal 9 and a pocket opening 10 so that, as shown in FIG. 3A–3C the entire bag strip which includes the used sponges can be rolled into a cylinder 23 and then tucked into the bag 19 as shown in FIGS. 3A–3C or similar receivers as shown in FIGS. 4A–4B to 9A–9B.

It will be recognized that in the arrangements shown in FIGS. 1A–1B the openings 10 of pockets 8 face in the same direction as the openings of the bags 1. However, in the arrangements shown in FIGS. 3A–3C the pocket is initally on the opposite side of the strip assembly from the sponge receiving pockets but the principal of operation is the same because the pocket is flipped to the side to receive the roll 23 whereby in the embodiment shown in the procedure illustrated in FIGS. 3A, 3B the receptacle 19 is effectively turned inside out to be positioned as shown in FIG. 3B to receive the roll 23 as shown in FIGS. 3C.

Figure 2A:
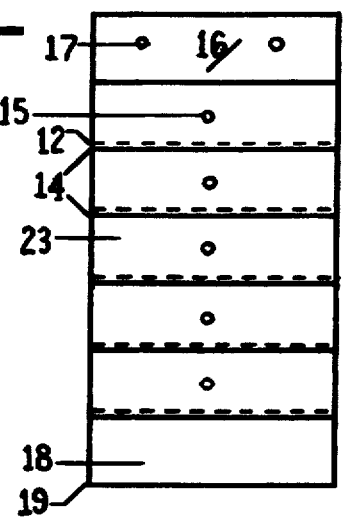
FIGS. 2A–2B illustrate another arrangement within the scope of the present invention.
Figure 2B:
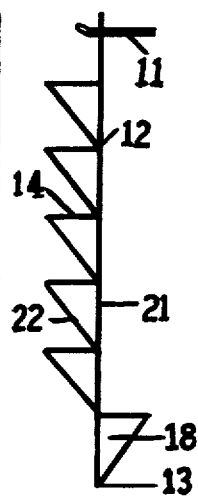

In FIGS. 2A–2B the bag strip is provided having an upper panel 16 with holes 17 similar to the holes 7 of the apparatus of FIGS. 1A, 1B. The bag pockets are defined by slits 14 and seals 12. Openings 22 of the pockets are shown in FIG. 2B. In the arrangement shown the receptical 18 is provided on the side opposite the sponge receiving pockets 22 so that the device can be operated as shown in FIGS. 3A–3C.

It will be understood that within the scope of the present invention the entire assembly can be defined by over lying planar strips of material where the pockets which are sealed on the side. The pockets are formed by slits 4 and 14 of FIGS. 1A–1B to 2A–2B allow access to the area between the planar layers.

Figure 4A:
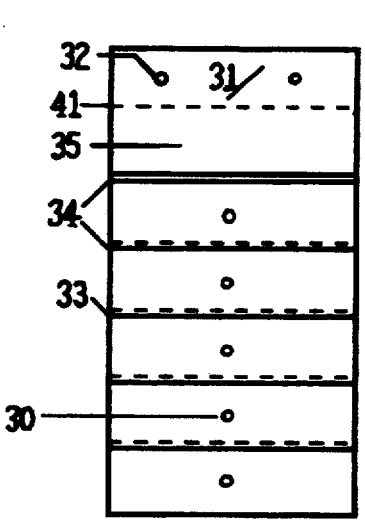
FIGS. 4A–4B illustrate yet another arrangement within the scope of the present invention.
Figure 4B:
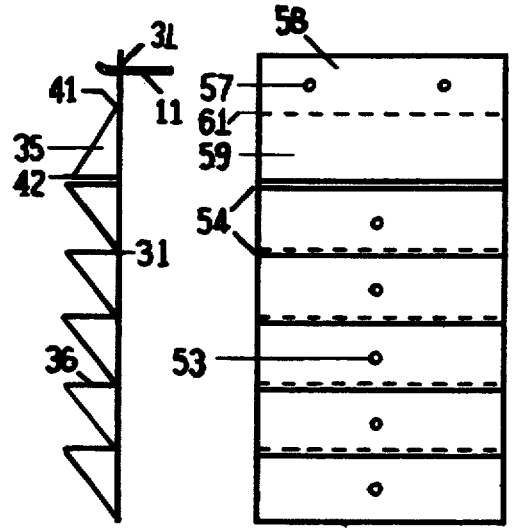

FIGS. 4A, 4B illustrate yet another arrangement within the scope of the present invention. In this case the pockets 29 are provided as previously described with welds 30 located to define two pockets in each pocket strip. The retainer panel 31 is provided having holes 32 to receive a support similar to the support 11 of the arrangements shown in FIGS. 1A, 1B. However in this arrangement the receptacle 35 is located above the section which defines the pockets and as shown pocket 35 is defined having its opening 42 facing the sponge receptacle pockets having openings 36 with lowers seals 33. When the devide has been completely filled with sponges it can be rolled and inserted into the openings 42 of pocket 35 same as shown in FIGS. 3A–3C.

Figure 5A:
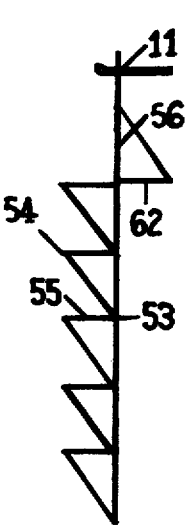
FIGS. 5A–5B illustrate yet another arrangement within the scope of the present invention.
Figure 5B:
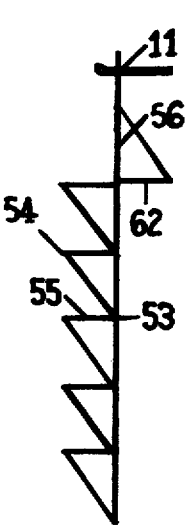

Another arrangement within the scope of the present invention is shown in FIGS. 5A, 5B. In FIGS. 5A, 5B the arrangement is similar to that shown in FIGS. 4A, 4B except that a receptacle 59 is provided having an opening 62 which is on the side of the assembly opposite the opening to the bag sections. Each pocket is defined by a slit 54 which provides the opening 55 and a seal 53.

The arrangement shown in FIG. 5A, 5B is operated similar to that described and shown in FIGS. 3A, 3C. That is the bag strip is rolled upward to the end of the device and then the pocket 59 is reversed to the top side forming the pocket 59 on top of the planar device so that the rolled up pockets can be tucked into the pocket for storage.

The arrangements shown in FIGS. 6A, 6B illustrate an assembly within the scope of the present invention where pockets 70 are provided which open upwardly as shown in FIG. 6B and have openings 74 corresponding to the slits 74 where a seal 72 is provided to define the bottom of each pocket. The receiving pocket 78 is located at the bottom of the assembly having one end defined by the seal 72A and opening 79 to receive the rolled device including the used sponges. It will be understood that in the arrangement shown the pocket 78 is reversed in order to receive the rolled sponges in the pockets similar to the method illustrated in FIGS. 3A–3C.

FIGS. 7A and 7B illustrate yet another arrangement in accordance with the present invention where pockets 80 are provided having openings defined by the slits 84 and the bottoms defined by seals 82.

The receiving pocket 88 is located at the bottom of the assembly but on the side of the device opposite the sponge receiving pockets 80.

Likewise FIGS. 8A and 8B illustrate yet another arrangement within the scope of the present invention where pockets 90 are defined having openings defined by slits 94 and bottoms defined by seals 92. The receiving pocket 98 is provided at the top of the assembly having an opening 99 on the same side of the device as pockets 98. FIG. 9A is an illustration of an arrangement within the scope of the present similar to that shown in FIGS. 8A and 8B where sponge receiving pockets 100 are provided with an opening defined by a slit 104 and defined by seal 102. The receiving pocket 108 is provided on the opposite side of the assembly as shown.

Figure 10A:
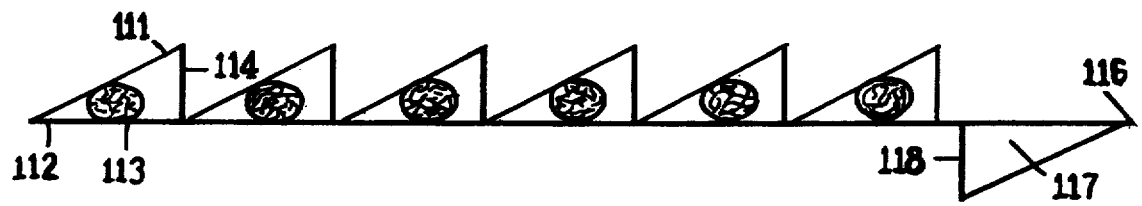
FIGS. 10A–10D illustrates one example of the operation of a device within the scope of the present invention.
Figure 10B:
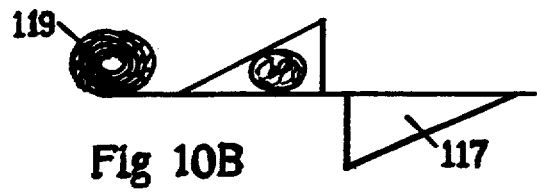

FIGS. 10A–10B illustrate in more detail the operation of a device of the type shown in 9A–9B.

In FIG. 10A a base 112 is shown where pockets 111 are provided having openings 114. Used Sponges 113 are shown located in the pockets. In the arrangement shown the receving pockets 117 have an opening 118 located on the side of base 112 opposite the pocket 111.

Figure 10C:
Figure 10D:
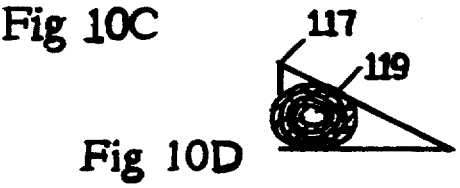

FIG. 10B is an illustration of the beginning of a procedure for removal of a used package where the pockets 111 the base 112 and the sponges 113 have been rolled into a roll 119 as shown. In FIG. 10C the pocket 117 has been turned to the top of the base 112 as shown. In this case the segment 116 which receives the support members has been turned into the pocket 117 whereby in the embodiment shown in the procedure illustrated in FIGS. 10A, 10B the receptacle 117 is effectively turned inside out to be positioned as shown in FIG. 10B to receive the roll 119 as shown in FIG. 10C. In FIG. 10D the roll has progressed to the point where the entire roll 119 is received within the pocket 117 for disposal.

Figure 11A:
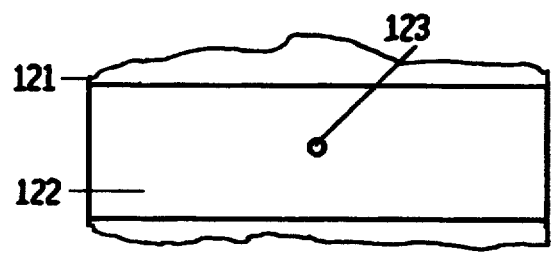
FIGS. 11A–11B illustrate arrangements to separate pockets in devices within the scope Of the present invention.

FIGS. 11A and 11D illustrate methods of dividing the larger pockets as shown in the previous Figures into the smaller pockets. In FIG. 11A the pocket 122 is shown on a base 121 a weld 123 is provided as shown for applications where a larger sponge might be used and the weld broken to insert a larger sponge.

Figure 11B:
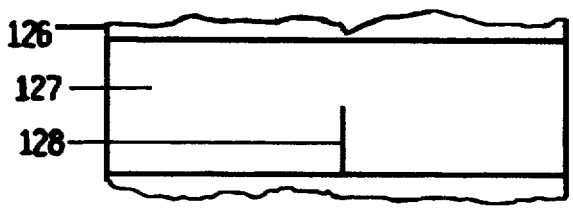

In FIG. 11B a seal 128 is used which extends partially up the depth of a pocket 127 which is located on the base 126 as previously described.

In the arrangement shown in FIG. 11A the seal divides the pocket so that either side can be utilized for a smaller sponge or a larger sponge can be still be inserted into the pocket without breaking through the wall of the pocket.

The latter case retains the ability to have separated sponges for accounting or a larger sponges for accounting without manipulating the pocket.

It has been found that devices within the scope of the present invention provide a highly effective means for preventing the loss of the blood contained in the sponges during the storage procedure. At this time any reduction in exposure to blood is benefical in the reduction of the likelihood of illiness due to exposure to infectious diseases.

It will be understood that the foregoing are but a few examples of arrangements within the scope of the present invention and other arrangements also within the scope of the present invention will occur to those skilled in the art upon reading the disclosure set forth hereinbefore.

The invention claimed is:

1. A bag strip including a series of sponge receiving pockets for soiled surgical sponges including: superposed first and second flat flexible panels; connecting means to join said first and second panels together along a portion of the periphery of both to form said bag strip; slit means in said first panel extending transverse to a longitudinal axis of of said bag strip to form mouth means of a pocket of said bag section where each said mouth means faces toward a first end of said bag strip; seal line means extending generally transverse to said longitudinal axis in spaced relation from said mouth means to join said first and second panels to form a bottom for each said pocket; receptacle means located at one end of said bag strip and having an opening located on the side of said strip opposite the side on which said mouths of said pockets are located so said strip can be rolled and inserted into said receptacle means.

2. The invention of claim 1 wherein said opening to said receptacle faces said first end of said bag strip.

3. The invention of claim 1 wherein said opening to said receptacle faces the end of said strip opposite said first end.

4. The invention of claim 1 including hanger means on the same end of said bag strip as said receptacle means.

5. The invention of claim 1 including hanger means located on the end of said bag strip opposite said receptacle means.

6. The invention of claim 1 wherein said pockets include selectively rupturable joint means between said first and second panels to divide selected pockets into pocket segments.

7. The invention of claim 6 wherein said rupturable connection is a spot weld located to connect said first and second panels in said pocket.

8. The invention of claim 6 wherein said rupturable connection is a generally continuous weld extending from adjacent said mouth means toward said seal means of said pocket.

* * * * *